(12) United States Patent
Green et al.

(10) Patent No.: US 8,114,003 B2
(45) Date of Patent: Feb. 14, 2012

(54) METHODS FOR HEMOLYSIS DETECTION IN CENTRIFUGAL BLOOD SEPARATOR

(75) Inventors: Todd Curtis Green, Lakewood, CO (US); Bruce W. Gibbs, Arvada, CO (US)

(73) Assignee: CaridianBCT, Inc., Lakewood, CO (US)

( * ) Notice: Subject to any disclaimer, the term of this patent is extended or adjusted under 35 U.S.C. 154(b) by 402 days.

(21) Appl. No.: 12/423,883

(22) Filed: Apr. 15, 2009

(65) Prior Publication Data
US 2010/0267538 A1 Oct. 21, 2010

(51) Int. Cl.
*B04B 15/00* (2006.01)
(52) U.S. Cl. .............................. 494/37; 494/10; 604/4.01
(58) Field of Classification Search ................. 494/1, 10, 494/37, 45; 604/4.01–6.16
See application file for complete search history.

(56) References Cited

U.S. PATENT DOCUMENTS

| 4,305,659 A * | 12/1981 | Bilstad et al. .................... 356/40 |
|---|---|---|
| 5,734,464 A | 3/1998 | Gibbs |
| 5,936,714 A | 8/1999 | Gibbs |
| 6,200,287 B1 | 3/2001 | Keller et al. |
| 6,537,445 B2 * | 3/2003 | Muller .............................. 494/1 |
| 6,773,413 B2 | 8/2004 | Keller et al. |
| 7,052,606 B2 | 5/2006 | Gibbs et al. |

OTHER PUBLICATIONS

U.S. Appl. No. 12/234,960, filed Dec. 26, 2007, Fender et al.

* cited by examiner

*Primary Examiner* — Walter D Griffin
*Assistant Examiner* — Timothy Cleveland
(74) *Attorney, Agent, or Firm* — John R. Merkling; Edna M. O'Connor; Laura B. Arciniega

(57) ABSTRACT

A centrifugal blood processing apparatus comprising a centrifuge rotor, a separation chamber, a tubing set for conducting blood components and fluids and having an inlet line, and an outlet line. Apparatus tests flow conditions using a red light-green light sensor to detect non-recoverable hemolysis during priming by identifying a high R/G ratio, preferably a ratio of greater than or equal to fifty (50), prior to the beginning of the first return of blood components to a donor followed by identifying a R/G ratio at least as great as one and one tenth (1.1) together with a green signal less than a predetermined value, preferably less than or equal to one thousand (1000) reflectance units. If these conditions are detected, an alarm is given and the apheresis procedure is discontinued.

5 Claims, 7 Drawing Sheets

METHODS FOR HEMOLYSIS DETECTION IN CENTRIFUGAL BLOOD SEPARATOR

FIELD OF INVENTION

The present invention relates generally to the field of extracorporeal blood processing methods and apparatus which are particularly useful in blood component collection, and more particularly, the present invention relates to methods and apparatus for the detection of hemolysis in a centrifugal blood separator, preferably an aphaeresis system.

BACKGROUND OF THE INVENTION

One well-known type of extracorporeal blood processing involves an aphaeresis system and procedure in which blood is removed from a donor or a patient (hereafter referred to as a donor), directed to a blood component separation device (e.g., centrifuge), and separated into various blood component types (e.g., red blood cells, white blood cells, platelets, plasma) for collection or therapeutic purposes. Some of these blood component types may either be collected or may be treated for therapeutic purposes and returned to a donor, while the remainder may simply be returned to the donor. Representative centrifugal blood processing systems are the Trima (trademark) and Trima Accel (trademark) aphaeresis machines available from CaridianBCT. Features of these systems are described in US patents and patent applications including, for example, U.S. Pat. Nos. 7,052,606, and 6,773,413, and 6,200,287, and U.S. application Ser. No. 12/234,960.

A number of factors may affect the commercial viability of an aphaeresis system. One factor relates to the time and expertise required of an individual to prepare and operate the aphaeresis system. For instance, reducing the time required by the operator to complete an entire collection procedure, as well as reducing the complexity of these actions, can increase productivity or lower the potential for operator error. Moreover, reducing the dependency of the system on the operator may further lead to reductions in the credentials desired/required for the operators of these systems. Characteristics of the fluids during the collection process may be sensed by various sensors in order to automate the separation process, as far as possible. An exemplary sensor illuminates a tube transporting fluid and detects ratios of reflected or transmitted red and green light from the fluid. The presence of red blood cells can be detected. Such a sensor is described in U.S. Pat. No. 5,734,464. Nevertheless, accurate and consistent control of a high-speed centrifugal blood separation system is difficult and complex, and further improvement in the control of possible failure modes is desirable.

SUMMARY OF THE INVENTION

The present invention generally relates to extracorporeal blood processing, and in particular, to improved sensing and control during priming of a blood processing machine. "Priming" refers to the process of preparing a blood processing machine for the separation process and includes loading the machine with fluid. The initializing fluid may be saline solution or some other fluid. In certain machines, such as the Trima Accel machine, the donor's blood may be used for the priming procedure. Since each of the various aspects of the present invention may preferably be incorporated into an aphaeresis system (e.g., whether for blood component collection in which "healthy" cells or other blood components are removed from the donor blood for later transfusion, or for therapeutic "unhealthy" blood component removal), the present invention will be described in relation to such aphaeresis systems. Aphaeresis may often imply the return of certain blood components back to the donor. However, certain aspects of the present invention may be suited for extracorporeal blood processing applications in which all donated blood components are retained and such are also intended within the scope of the present invention.

An aphaeresis system which may be used with one or more aspects of the present invention generally includes at least a blood component separation device, which provides the mechanism and/or the forces required to separate blood into various blood component types, such as red blood cells, white blood cells, platelets, or plasma. In one preferred embodiment, the separation device includes a centrifuge channel which receives a disposable blood processing vessel. Typically, a donor or perhaps a patient (collectively referred to hereafter as a donor) is fluidly interconnected with the blood processing vessel by an extracorporeal tubing circuit, and preferably the blood processing vessel and extracorporeal tubing circuit collectively define a closed, sterile system. When the fluid interconnection is established, blood may be extracted from the donor and directed to the blood component separation device such that at least one type of blood component may be separated and removed from the blood, either for collection or for therapy. An additive/storage solution is added to the red blood cells or platelets after collection. A blood return reservoir has heretofore been used to receive selected blood components before returning those components to the donor.

During priming and other steps of a blood component separation procedure, certain conditions should be detected and corrected or reported to the operator or both. Among the undesirable conditions are spillover and hemolysis. Spillover is a condition wherein red blood cells escape from behind a barrier or dam in a separation vessel and mingle with separated platelets or plasma in an improper area of the separation vessel. Hemolysis occurs when some of the donor's red blood cells are broken, allowing free hemoglobin to be released into the plasma. In both conditions the expected relatively clear plasma is discolored by the presence of either red blood cells or hemoglobin. It is an object of the present invention to distinguish between spillover and hemolysis, particularly during blood prime, and to initiate appropriate corrective actions or warnings.

This invention uses the detected red-green ratio in a new way to distinguish a hemolysis condition during priming. Hemolysis will produce a reddish discoloration in the separated plasma as a consequence of the free hemoglobin released into the plasma. "Spillover", a condition wherein a few red blood cells may spill over a barrier in the separation vessel, may allow sufficient numbers of red blood cells to enter the platelet line where they may be detected by the red-green sensor. It is important, therefore, to distinguish between the non-recoverable condition of hemolysis and the correctable condition of spillover.

Prime hemolysis events have high R/G (red/green) ratio values. Prime hemolysis events do not resolve themselves and present an R/G ratio that persists into early run phases of a separation procedure, potentially triggering spillover alarms. Further, hemolysis events during priming appear to be accompanied by a characteristic signal in terms of the R/G ratio and the absolute value of the Green light intensity signal. High R/G ratio values also occur for a relatively small number of self-recovering prime spillovers and these values statistically overlap the R/G ratio range for hemolysis events during priming. In addition, high R/G ratio values may be caused by events other than hemolysis or spillover, such as by centrifuge stop or by operator-initiated termination of the blood processing procedure.

The apparatus of this invention identifies non-recoverable hemolysis during priming by identifying a high R/G ratio, preferably a ratio of greater than or equal to fifty (50), prior to the beginning of the first return of blood components to the donor followed by identifying a R/G ratio at least as great as one and one tenth (1.1) together with a green signal less than a predetermined value, preferably less than or equal to one thousand (1000) reflectance units. If these conditions are detected, an alarm should be given and the apheresis procedure should be discontinued. It is believed that this process would allow an apparatus both to avoid false positives, that is, a recoverable priming spillover falsely identified as hemolysis, and to avoid false negatives, that is, not recognizing a hemolysis event, with high confidence.

These and still further aspects of the present invention are more particularly described in the following description of the preferred embodiments presented in conjunction with the attached drawings which are described briefly below.

DETAILED DESCRIPTION

The present invention will be described in relation to the accompanying drawings. Generally, the present invention relates to improvements for a blood processing aphaeresis system.

Figure 1:
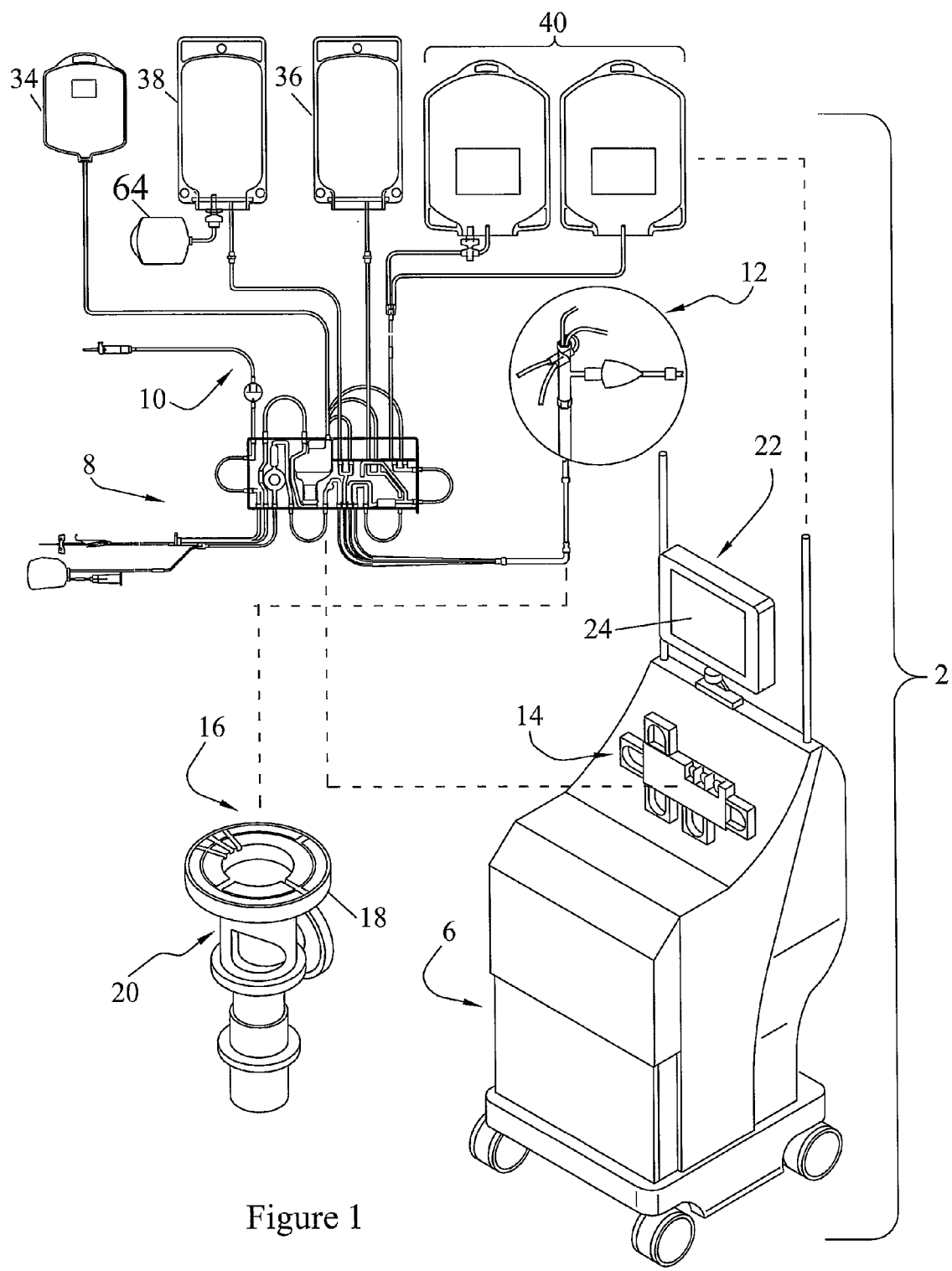
FIG. 1 is a schematic view of an aphaeresis system.

A preferred blood aphaeresis system 2 for use in and/or with the present invention is schematically illustrated in FIG. 1. System 2 preferably provides for a continuous blood component separation process. Generally, whole blood is withdrawn from a donor and is substantially continuously provided to a blood component separation device 6 where the blood is continuously separated into various component types and at least one of these blood component types is collected from the device 6. One or more of the separated blood components may then either be provided for collection and subsequent use by another through transfusion or may be uncollected and then returned to the donor. Therapeutic treatment and near immediate return of certain separated blood components is a viable, yet less common alternative use as well. It is also understood that for therapeutic treatment the blood may be separated into components with filtration using the principles of the instant invention and as described below at a patient's bedside for return to such patient.

In the blood aphaeresis system 2, blood is withdrawn from the donor and directed through a pre-connected bag and tubing set 8 which includes an extracorporeal tubing circuit 10 and, in one embodiment, a blood processing vessel 12 which together define a closed, sterile and disposable system. The set 8 is adapted to be mounted on the blood component separation device 6. The separation device 6 preferably includes a pump/valve/sensor assembly 14 for interfacing with the extracorporeal tubing circuit 10, and a channel assembly 16 for interfacing with the disposable blood processing vessel 12.

The channel assembly 16 may include a channel housing 18 that is rotatably interconnected with a rotatable centrifuge rotor assembly 20, which provides the centrifugal forces required to separate blood into its various blood component types by centrifugation. The blood processing vessel 12 may be fitted within the channel housing 18. When connected as described, blood can be flowed substantially continuously from the donor, through the extracorporeal tubing circuit 10, and into the rotating blood processing vessel 12. The blood within the blood processing vessel 12 may then be continuously separated into various blood component types and at least one of these blood component types (platelets, plasma, or red blood cells) may be removed from the blood processing vessel 12. Blood components which are not being retained for collection or for therapeutic treatment are preferably also removed from the blood processing vessel 12 and returned to the donor via the extracorporeal tubing circuit 10. Various alternative aphaeresis systems (not shown) may also make use of the present invention, including batch processing systems (non-continuous inflow of whole blood or non-continuous outflow of separated blood components) or smaller scale batch or continuous RBC/plasma separation systems, whether or even if no blood components may be returned to the donor.

Operation of the blood component separation device 6 is preferably controlled by one or more processors included therein, and may advantageously comprise a plurality of embedded computer processors to accommodate interface with ever-increasing PC user facilities (e.g., CD ROM, modem, audio, networking and other capabilities). In order to assist the operator of the aphaeresis system 2 with various aspects of its operation, the blood component separation device 6 may include a graphical interface 22 with an interactive touch screen 24.

Further details concerning the operation of an aphaeresis system, such as the Trima® System and the Trima® Accel™ System (available from the assignee of this application, CaridianBCT, Inc., formerly Gambro BCT, Inc., of Lakewood, Colo.) may be found in a plurality of publications, including, for example, U.S. Pat. No. 5,734,494, U.S. Pat. No. 7,052,606, U.S. Pat. No. 6,773,413, and U.S. Pat. No. 6,200,287, and U.S. application Ser. No. 12/234,960. The disclosures are incorporated herein. A plurality of other known aphaeresis systems may also be useful herewith, as for example, the Baxter CS3000®, Amicus®, Autopheresis-C®, and Alyx systems or the Haemonetics MCS® and MCS®+, or the Fresenius COM.TEC™ and AS-104™ or like systems.

Figure 2:
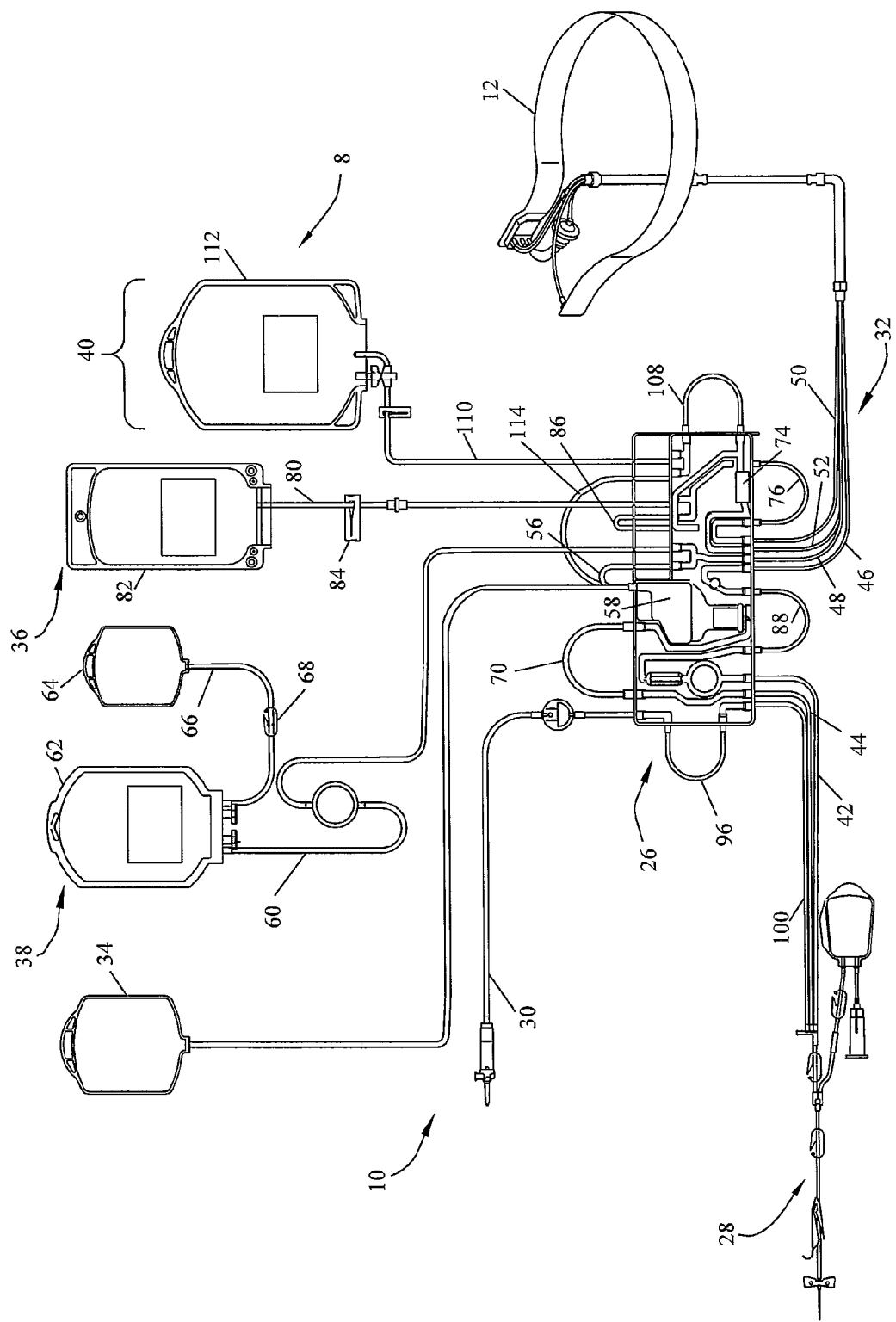
FIG. 2 illustrates a tubing and bag set including an extracorporeal tubing circuit, a cassette assembly, and collection bag assembly for use with the system of FIG. 1.

As illustrated in FIG. 2, the pre-connected extracorporeal tubing circuit 10 is shown which may include a cassette assembly 26 and a number of tubing/collection assemblies 28, 30, 32, 34, 36, 38 and 40 interconnected therewith. A blood removal/return tubing assembly 28 provides a single needle interface between a donor and the remainder of the tubing circuit 10 (although a two-needle set-up, not shown, may also be used). At least two lines 42, 44 are provided in assembly 28 for removal of blood from and return of components to the donor. This embodiment includes a cassette assembly 26, which is connected between the blood removal/return tubing assembly 28, and a blood inlet/outlet tubing assembly 32, which provides the coupling between cassette assembly 26 and blood processing vessel 12. Four lines 46, 48, 50 and 52 are shown in FIG. 2 for transport of blood, blood components and other fluids to and from the processing vessel 12. An anticoagulant tubing assembly 30, a plasma collection assembly 36, a red blood cell collection assembly 38, a vent bag tubing line assembly 34, and a platelet assembly 40 are also interconnected with cassette assembly 26 in this embodiment. The extracorporeal tubing circuit 10 and blood processing vessel 12 are preferably pre-connected as a closed, pre-sterilized, disposable assembly for a single use.

An PBC (red blood cell) outlet tubing line 48 of the blood inlet/blood component tubing assembly 32 connects the processing vessel 12 with an RBC return tubing loop 56 to return separated RBCs to a donor. For such purpose, the RBC return tubing loop 56 is preferably connected to the top of a blood return reservoir 58 of the cassette assembly 26. The tubing line 48 may also be connected with an RBC collection tubing assembly 38 for collecting RBCs. RBC collection tubing and bag assembly 38 includes an RBC collector tubing line 60, an RBC collection reservoir or bag 62, and an air removal bag 64. The air removal bag 64 is attached to the RBC collection bag 62 by a tubing line 66 which may have an optional clamp 68 attached thereto.

Plasma tubing 50 of blood inlet/blood component tubing assembly 32 connects through an integral plasma passageway to a pump-engaging, plasma tubing loop 76. Through an integral plasma passageway, the plasma tubing loop 76 connects to the plasma collection tubing assembly 36 via tubing line 80. The plasma collection tubing assembly 36 may be employed to collect plasma during use and includes plasma collector tubing 80 and plasma collection bag 82. A slide clamp 84 may be provided on plasma collector tubing 80. The plasma tubing loop 76 is also connected to a plasma return tubing loop 86 to return plasma to donor/patient. For such purpose, the plasma return tubing loop 86 is connected through loops 108 and 114 to the top of the blood return reservoir 58 of the cassette assembly 26.

Platelet collect tubing 52 connects through an integral passageway past a red/green light sensor 74, described below, to a pump-engaging loop 108 and either to a return loop 114 connected to the reservoir 58 or to the platelet collection assembly 40. The platelet collection assembly 40 comprises a connecting tube 110 and one or more bags 112. A valve (not shown) in the cassette directs the collected platelets either to the return loop 114 or to the platelet collection assembly.

One or more types of uncollected blood components, e.g., red blood cells, plasma, or platelets (collectively referred to as return blood components) will cyclically accumulate in and be removed from reservoir 58 during use. Here also, valve/clamp access is made through cassette assembly 26 to maintain the plasma collector tubing 80 and plasma return tubing loop 86 in a predetermined spaced relationship for flow control therethrough.

Most portions of the tubing assemblies 28, 30, 32, 36, 34, 38, and 40 and cassette assembly 26 are preferably made from plastic components including, for example, polyvinyl chloride (PVC) tubing lines, that may permit visual observation and monitoring of blood/blood components during use. It should be noted that thin-walled PVC tubing may be employed for approved, sterile docking (i.e., the direct connection of two pieces of tubing line) for the RBC collector tubing lines 60, inter alia. All tubing lines are pre-connected before sterilization of the total disposable assembly to assure that maximum sterility of the system is maintained. A highly desirable advantage of pre-connection of all of the elements of the tubing circuit including the collection bag sub-assembly 38 involves the complete pre-assembly and then sterilization hereof after pre-assembly such that no sterile docking is later necessary (spike addition of storage solution excepted). Thus, the costs and risks of sterile docking are eliminated. Alternatively, thicker-walled PVC tubing may be employed for approved, sterile docking RBC collector tubing lines 60, inter alia.

As mentioned, a cassette assembly 26, may be mounted upon and operatively interface with the pump/valve/sensor assembly 14 of a blood component separation device 6 during use. Further details of an aphaeresis system set-up including the loading and interaction of a disposable assembly 8 with a blood component separation device 6, may be found in the above-listed patents, inter alia, and are not exhaustively repeated here.

Except as expressly set forth herein, operations of the aphaeresis process are preferably carried out as set forth in the above-listed patents. During a blood removal, whole blood will be passed from a donor into tubing line 44 of blood removal/return tubing assembly 28 and is then transferred to blood component separation device 6. At device 6, the blood is pumped via loop 88, to the processing vessel 12 via the cassette assembly 26 and inlet line 46 of the blood inlet/blood component tubing assembly 32. Separation processing then occurs on a substantially continuous basis in vessel 12; i.e., blood flows therein, is separated and flows as separated components therefrom. After separation processing in vessel 12 (though separation is continuously occurring), uncollected blood components are transferred from the processing vessel 12 to and through cassette assembly 26, into and may then accumulate in reservoir 58 of cassette 26 up to a predetermined level at which the blood component separation device 6, in a single needle operation, may (though in a continuous system, need not) pause the blood removal and initiate a blood return wherein these uncollected and/or treated components may be returned to the donor. As such, these accumulated components may be transferred through a pump-engaging loop 70 into the blood return tubing line 44 of blood removal/return tubing assembly 28 and back into the donor. During the single needle blood return, when the accumulated return blood components in reservoir 58 are removed down to a predetermined level, blood component separation device 6 will then automatically end the blood return. This preferably will also automatically serve to reinitiate or continue the blood removal. The cycle between blood removal and blood return will then continue until a predetermined amount of collected blood components have been harvested. In an alternative dual needle scheme, as is known in the art, blood may be continually removed from and blood components continually returned to a donor. The detailed mechanisms for such operations, including controlling the pumps, for example, are not shown or described in detail herein.

Also, certain components may be collected simultaneously or consecutively one after the other. In one example, platelets may be collected prior to collection of RBCs while plasma may be collected concurrently with either. In the primary example shown, three components are collected: RBCs in the RBC sub-assembly 38 and plasma in assembly 36 and platelets in the other collection assembly 40. When a sufficient quantity of one or the other is collected, further separated portions of such a component are returned to the donor with any other uncollected components, until a sufficient quantity of all components are collected. One or two selected components may be collected with all other components being returned to the donor.

In normal operation, whole blood will pass from the donor through the needle and blood removal tubing assembly 28, cassette assembly 26 and blood inlet tubing line 46 to processing vessel 12. The whole blood will then be separated in vessel 12. Also, a platelet stream or a plasma stream may be separated herein and be either collected in a collector assembly 40 or 36, or diverted to reservoir 58 for ultimate return to the donor. Separated plasma may be flowed through cassette 26 via loop 76 and line 86 for collection in the container 82 for plasma or diverted to reservoir 58. Separated platelets may be flowed through cassette 26 past red/green light sensor 74 via loop 108 and line 110 for collection in the containers 112*a*, 112*b* or diverted to reservoir 58 through loop 114. Further, red blood cells (including potentially some white blood cells) may be separated in and passed from vessel 12 through RBC outlet tubing line 64, through cassette assembly 26 and, in return mode, into reservoir 58. In a preferred alternative, during an RBC collection procedure separated RBCs will be delivered to RBC collector tubing and bag assembly 38 through tubing line 60 for collection.

One preferred protocol, which may be followed for performing an aphaeresis procedure relative to a donor utilizing the described system 2, will now be summarized. Initially, an operator loads the disposable plastic assembly 8 in and/or onto the blood component separation device 6. According hereto, the operator hangs the various bags on hooks on the blood component separation device 6. If one is used, the operator then also loads the cassette assembly 26 on the device 6 and/or the blood processing vessel 12 within the channel housing 18 as mounted on the centrifuge rotor assembly 20 in the machine 6.

With the extracorporeal tubing circuit 10 and the blood processing vessel 12 loaded in the described manner, the donor may then be fluidly connected with the extracorporeal tubing circuit 10 by inserting an access needle of the needle/tubing assembly 28 into the donor. In addition, the anticoagulant tubing assembly 30 is primed by passing anticoagulant solution from a bag (not shown through a pump-engaging loop 96 to a line 100, which adds controlled amounts of anticoagulant to the blood near the needle. The blood removal/return tubing assembly 28 is primed preferably with blood from the donor. The blood processing vessel 12 is also primed for the aphaeresis procedure. A blood prime may be used in that blood will be the first liquid introduced into the blood processing vessel 12. During the priming procedure, as well as throughout the remainder of the aphaeresis procedure, blood may be flowed into the vessel 12, blood components are separated from each other and one or more components is removed from the blood processing vessel 12. Further details on a general blood processing procedure are set forth in U.S. application Ser. No. 12/234,940.

Figure 3:
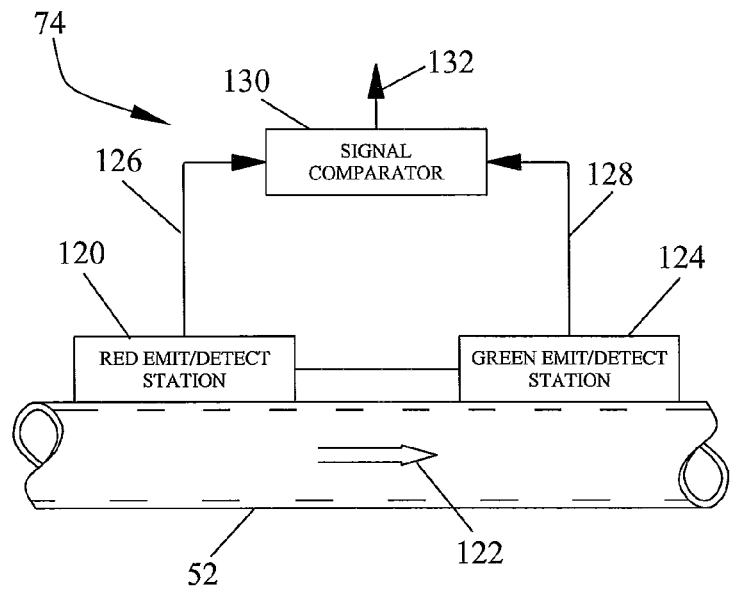
FIG. 3 shows a red-green detector for use in the aphaeresis system.

As shown in FIGS. 1 and 2, aphaeresis system 2 includes four relatively transparent tubes: blood component inlet tube 46 and collect tubes 48, 50 and 52. Collect tube 48 is intended to carry red blood cells. Plasma collect tube 50 carries plasma. Platelet collect tube 52 is intended to carry platelets, with the flow rate of the blood component within collect tube 52 typically in the range of from about 0.8 to about 25 ml/min. In FIG. 3, the direction of blood component flow is from left to right, as is shown by the arrows associated with platelet collect tube 52. In this embodiment, tubes 48, 46, 50 and 52 are constructed of optically transparent polyvinylchloride and are generally circular in cross section, and having an inner diameter of about 2.87 mm and an outer diameter of about 4.75 mm.

A red blood cell spillover detector 74 of the present invention is associated with platelet collect tube 52. While the physical spacing or distance that exists between detector 74 and blood processing vessel 12 is not critical, a utility of the present invention includes halting separation device 6 when red blood cells or hemolysis conditions are detected in platelet collect tube 52. Therefore, it may be desirable to keep the physical separation between detector 74 and separation vessel 12 at a minimum. In any case, the detector 74 includes light sources and mating light detector(s). In accordance with an important feature of the invention, both light sources and the mating light detector(s) that are within detector 74 are located on the same side of platelet collect tube 52.

Red light and green light are directed toward the blood collect tube that is to be monitored for the presence or spillover of red blood cells. As used herein, the term green light is intended to mean visible electromagnetic radiation having a wavelength of from about 4,912 to about 5,750 angstroms, and the term red light is intended to mean visible electromagnetic radiation having a wavelength of from about 6,470 to about 7,000 angstroms.

Detection of red and green light can occur during the same time interval, in which case two light sensors or light detectors are provided, one sensor being selectively responsive only to red light reflection and the other sensor being selectively responsive only to green light reflection. However, in a preferred embodiment, the two tests occur during two different but closely spaced time intervals. In this embodiment, only one sensor may be provided, this one sensor having a wide wavelength response so that it is responsive to red light reflection during one time interval, and is responsive to green light reflection during another time interval.

The magnitude of the red light reflection and the magnitude of the green light reflection are compared. In a preferred embodiment, the ratio of red light reflection magnitude to green light reflection magnitude is determined. A compare function that compares the ratio to a user supplied threshold value, which is the minimum spillover tolerated or lacking in adverse consequences for a given application.

FIG. 3 shows an embodiment of the detector 74 wherein platelet collect tube 52 has associated therewith a first emit/detect station 120 in accordance with the invention that operates to emit a first color of light (red) into collect tube 52, and then to detect the reflection of this first color from the blood component flow 122 within collect tube 52. Spaced a short distance from station 120 is a second emit/detect station 124 that operates to emit a second color of light (green) into collect tube 52, and then to detect the reflection of this second color from the blood component flow 122 within collect tube 52.

The two respective output conductors 126 and 128 of stations 120 and 124 carry electrical signals whose magnitudes are directly proportional to the magnitude of the reflected first light and to the magnitude of the reflected second light. An electrical signal comparator 130 operates to compare the two signals on conductors 126, 128, and to provide an output 126 as a result of this comparison.

The two stations 120, 124 may operate during the same time interval having duration of, for example, fractions of a second. In this case the two signals on conductors 126 and 128 also appear during this common time interval. Signal comparator 130 may or may not include a latch means (not shown) that saves the magnitudes of these two signals to enable a ratio calculation that takes advantage of the fact that red light reflection increases and green light reflection decreases as the concentration of red blood cells increases.

The two stations 120, 124 may also operate during two different time intervals that are spaced from one another. In this case, the two signals on conductors 126 and 128 also appear during these two different time intervals, and signal comparator includes a latch means (not shown) that saves the magnitudes of these two signals in order to enable the ratio calculation to be made after expiration of the later or second of the two time intervals.

While the physical spacing of the two stations 120, 124 along the length of collect tube 52 is not critical to the invention, it may be desirable to maintain this spacing to a minimum, and/or to time the later operation of station 124 relative to the earlier operation of station 120, as a function of the flow rate of the blood component within collect tube 52. In this way, both station 120 and station 124 operate on the same flowing volume of blood component 122.

Figure 4:
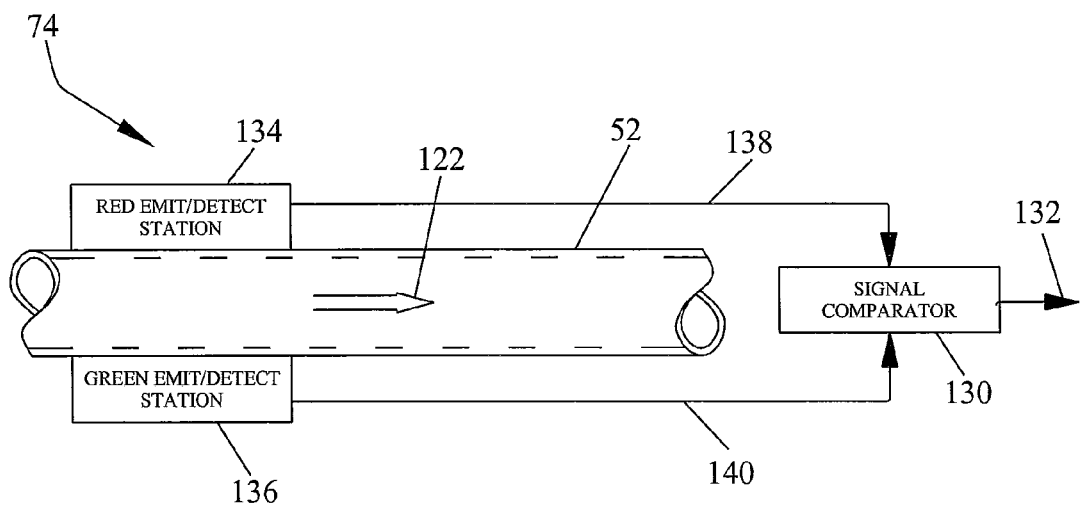
FIG. 4 shows a second configuration of the red-green detector of FIG. 3.

FIG. 4 shows an embodiment wherein platelet collect tube 52 has associated therewith a first emit/detect station 134 that emits a first color of light (red) into collect tube 52, and then detects the reflection of this first color from the blood component flow 122 within collect tube 52. Located diametrically across from station 134 is a second emit/detect station 136 that emits a second color of light (green) into collect tube 52, and then detects the reflection of this second color from the blood component flow 122 within collect tube 52.

Two respective output conductors 138 and 140 of stations 134 and 136 carry electrical signals whose magnitudes are directly proportional to the magnitude of the reflected first light and to the magnitude of the reflected second light. The electrical signal comparator 130 compares the two signals on conductors 138, 140, and provides an output 126 as a result of this comparison.

The two stations 134, 136 may operate during the same time interval, whereupon the two stations 134, 136 include individual light detectors that are selectively responsive only to the first light for the detector of station 134, and to the second light for the detector of station 136. In this case, the two signals on conductors 138 and 140 also appear during this time common interval. Comparator 130 may or may not include a latch means (now shown) to save the magnitudes of these two signals as the signal comparison is made. The two stations 134, 136 may also operate during two different time intervals. In this case, the light detector within each of the two stations 134, 136 is rendered operative only during the period of operation of that respective station 134, 136. Since interference is precluded by providing different time periods of operation for the two light detectors, the two light detectors may be of a relatively wide color response. The two electrical signals on conductors 138 and 140 also appear during these two different time intervals, and signal comparator 130 in this case includes a latch means (not shown) that operates to latch the magnitudes of these two signals 138, 140 in order to enable a comparison to be made after expiration of the later or second time interval.

The signal comparison provided at 130 is a ratio calculation, which takes advantage of the fact that red light reflection increases and green light reflection decreases as the concentration of red blood cells increases.

This invention uses the detected red-green ratio in a new way to distinguish a hemolysis condition during priming. Hemolysis occurs when red blood cells are broken, liberating hemoglobin into the surrounding fluid, for example, into plasma. Hemolysis may be caused by the effects of bacterial toxins, venoms, immune bodies, hypotonic solutions, or mechanical trauma. When hemolysis occurs within the blood vessels, the body is unable to retain hemoglobin, which is lost through the kidneys. In the context of an apheresis blood processing system, the observation of hemolysis, for whatever cause, should be considered as a condition requiring prompt or immediate termination of the apheresis process.

Hemolysis will produce a reddish discoloration in the separated plasma as a consequence of the free hemoglobin released into the plasma.

At the same time, however, it is frequently the case that, while the initial separation conditions are being established, a few red blood cells may spill over a barrier in the separation vessel. This is not a condition that requires termination of the procedure, and is easily corrected by the operator or automatically by the apheresis machine. Nevertheless, "spillover" may allow sufficient numbers of red blood cells to enter the platelet line where they may be detected by the red-green sensor 74. It is important, therefore, to distinguish between the non-recoverable condition of hemolysis and the correctable condition of spillover. Because both conditions introduce red coloration into the platelet line 52, simply measuring the intensity of the red coloration, or of the red-green ratio, will not distinguish between the two conditions.

Figure 8:
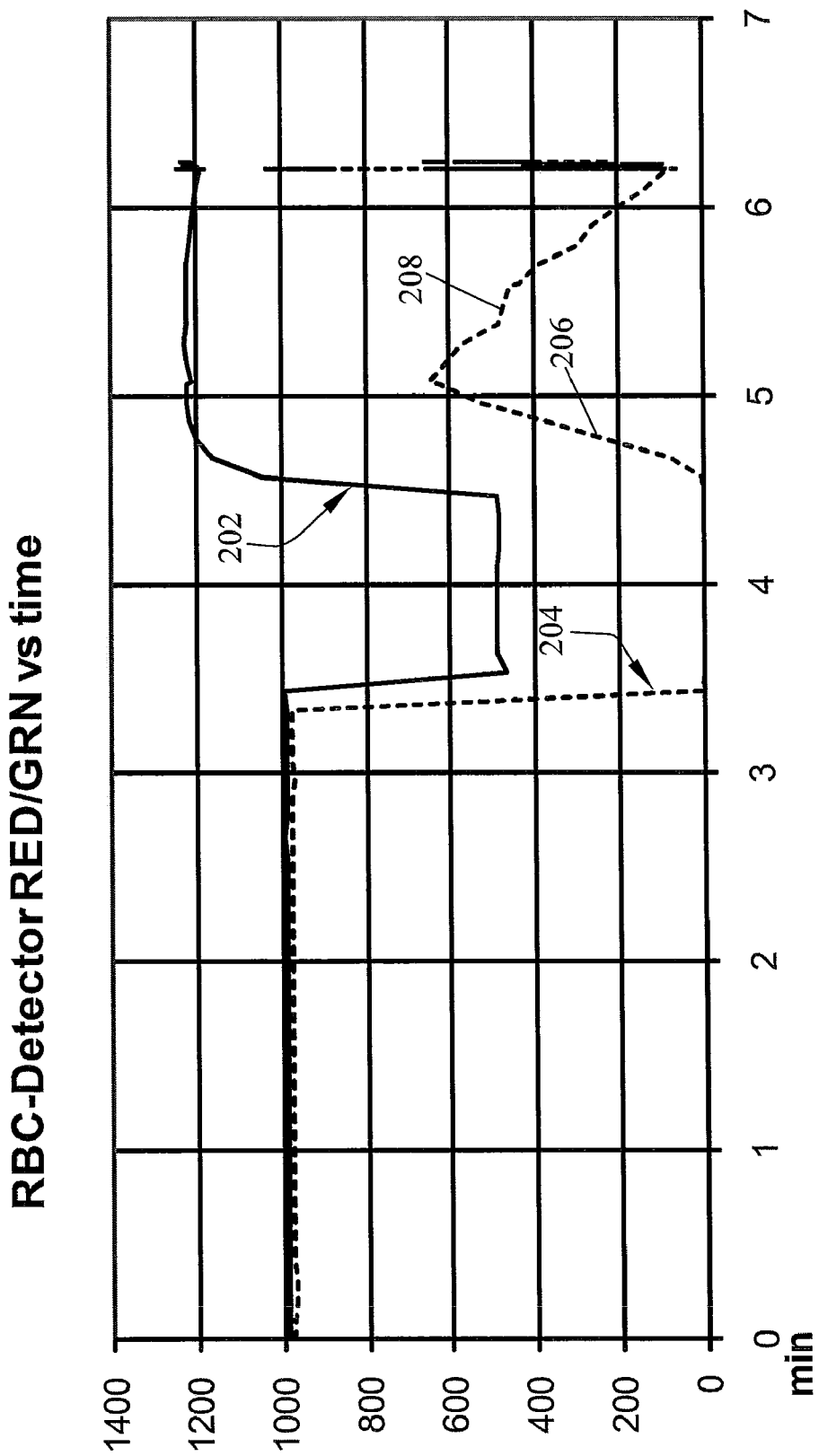
FIG. 8 is a graph of data.

FIG. 8 shows a graph of RED light intensity 202 and GREEN light intensity 204. The inventors believe that hemolysis events during prime, particularly events associated with mechanical trauma to red blood cells, are characterized by a repeated partial recovery 206 of the value of the GREEN light intensity 204, as detected by the red-green sensor 74, followed by a drop-off 208, as shown in the graph of FIG. 8. It is believed, therefore, that prime hemolysis events of this type have high R/G (red/green) ratio values. Prime hemolysis events do not resolve themselves and present an R/G ratio that persists into early run phases of a separation procedure, potentially triggering spillover alarms. Further, hemolysis events during priming appear to be accompanied by a characteristic signal in terms of the R/G ratio and of the absolute value of the Green signal. High R/G ratio values also occur for a relatively small number of self-recovering prime spillovers and these values statistically overlap the R/G ratio range for hemolysis events during priming. In addition, high R/G ratio values may be caused by events other than hemolysis or spillover, such as by centrifuge stop or by operator-initiated termination of the blood processing procedure.

Figure 5:
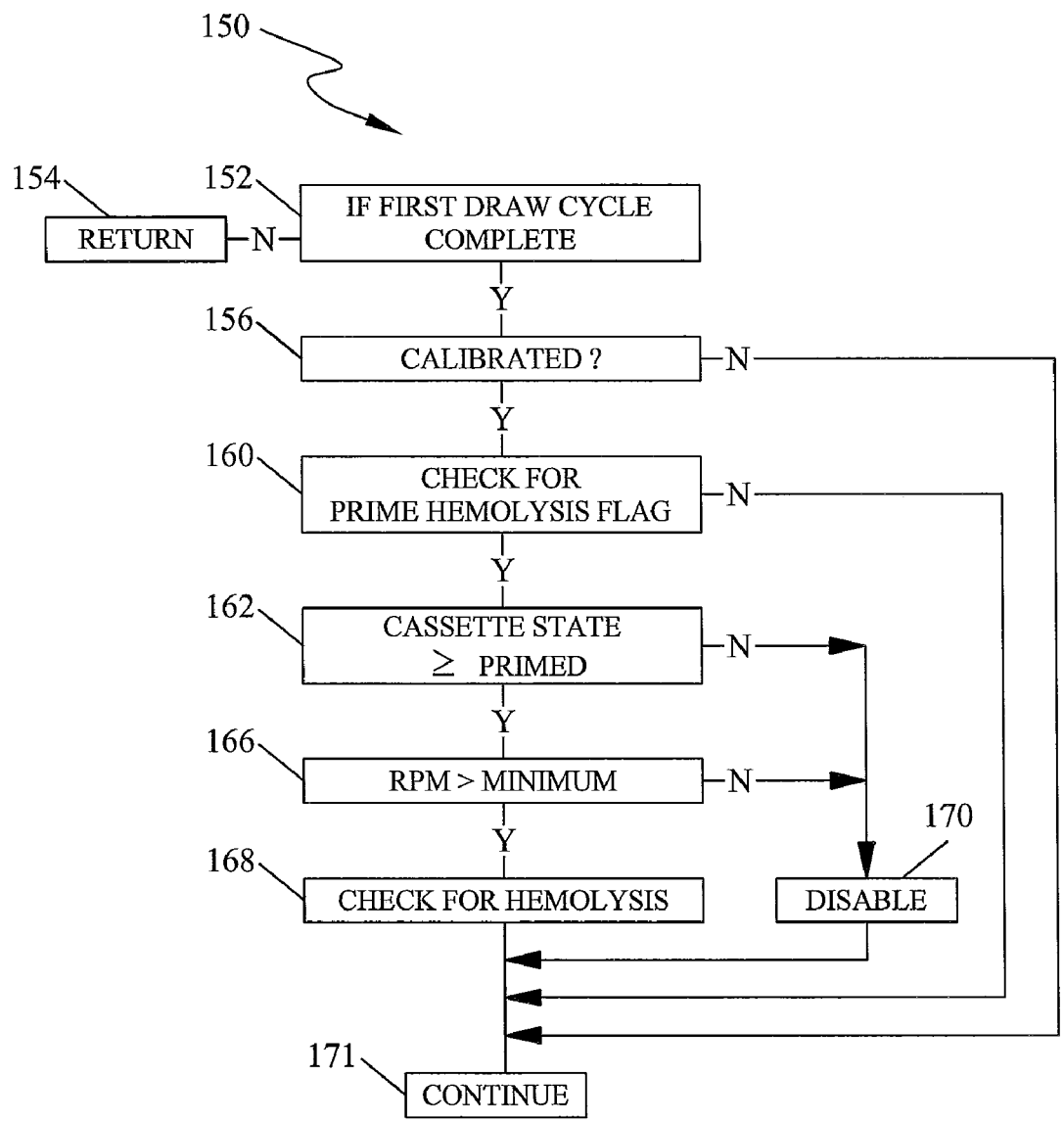
FIG. 5 shows a flow chart of a software implementation of a hemolysis test according to the present invention.
Figure 6:
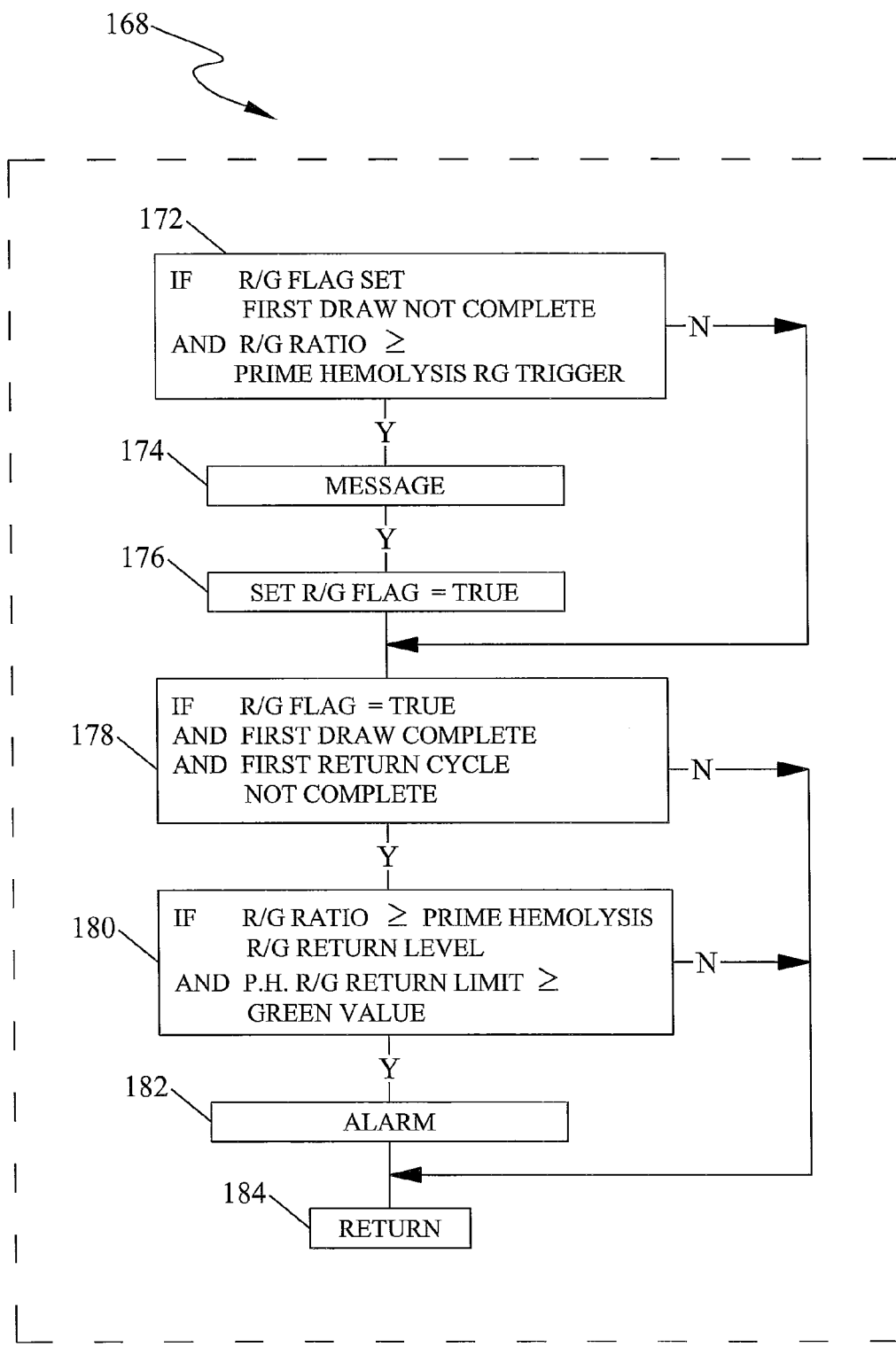
FIG. 6 illustrates a portion of the flow chart of FIG. 5, further describing the hemolysis test.
Figure 7:
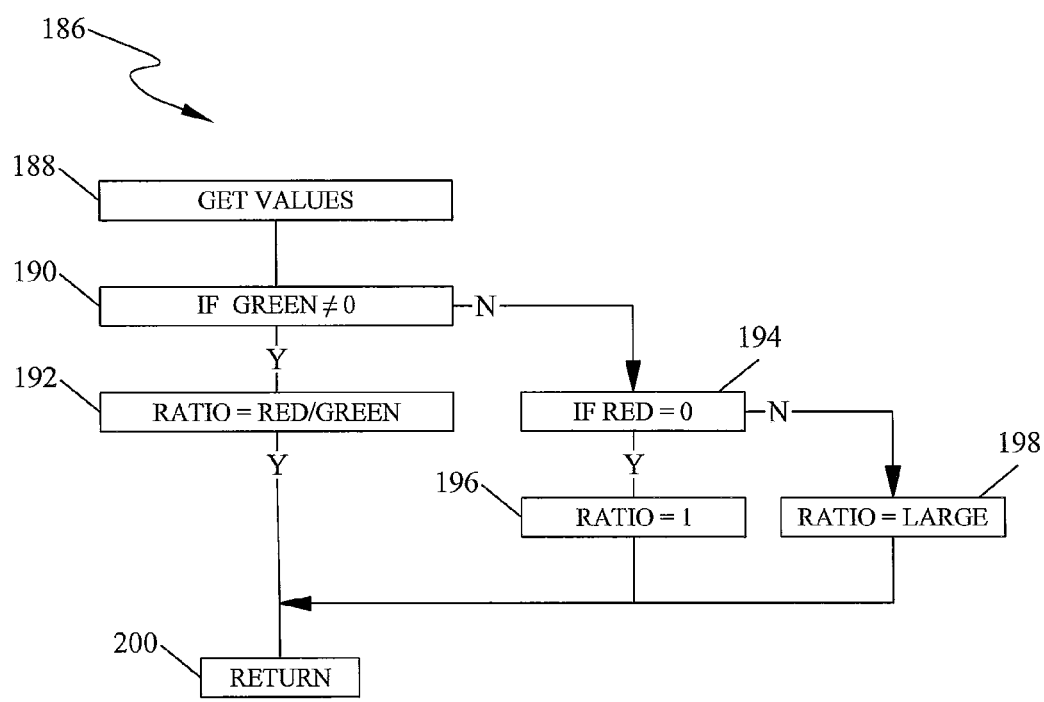
FIG. 7 shows a test for valid data from a red-green sensor.

The apparatus of this invention identifies non-recoverable hemolysis during priming by identifying a high R/G ratio, preferably a ratio of greater than or equal to fifty (50), prior to the beginning of the first return of blood components to the donor followed by identifying a R/G ratio at least as great as one and one tenth (1.1) together with a green signal less than a predetermined value, preferably less than or equal to one thousand (1000) reflectance units. If these conditions are detected, an alarm should be given and the apheresis procedure should be discontinued. It is believed that this process would allow an apparatus both to avoid false positives, that is, a recoverable priming spillover falsely identified as hemolysis, and to avoid false negatives, that is, not recognizing a hemolysis event, with high confidence. The process is illustrated in FIGS. 5, 6 and 7. Although the invention is described, for purposes of illustration, as a computer program, one skilled in the art would understand that the principles of the present invention could also be implemented in firmware or electronic hardware and such implementations should be considered as equivalents of the exemplary embodiment described herein.

FIG. 5 illustrates a prime hemolysis alarm program 150 for hemolysis detection during priming of an apheresis machine 2. The alarm program 150 is run as part of the initial programming at a frequency of about once every 0.5 seconds and before or during the first return cycle, that is, before or during the first attempt by the apheresis machine to return fluids to the donor. The apparatus checks 152 whether the first draw cycle (first removal of blood from the donor) has been completed. If the draw cycle has been completed, the apparatus can proceed with the hemolysis test during the first return cycle. If the first draw cycle has not been completed, the program returns 154 to other processes until the periodic return to this program, as described above. Otherwise, the apparatus determines 156 if the red/green sensor 74 has been calibrated. If not, the hemolysis check is skipped. Optionally, a flag may be set in the software to enable or disable the entire hemolysis test. Preferably, this flag should be accessible solely to a technician in connection with repair and maintenance of the machine. The apparatus, therefore, may check 160 the status of the flag to determine if the test should proceed. If the test is authorized, the apparatus inquires 162 for the state of the apheresis process. The state condition is maintained by other software programs and represents progressive steps or states of the blood processing procedure. For example, states may include "Enter donor data", "Load disposable collection unit", "Connect donor", "Prime", "Process blood", "Rinseback", ""Disconnect", and so on. If the state of the machine is beyond "Prime", that is, the priming process has been completed, the hemolysis test should not be performed, and the hemolysis alarm program 150 is disabled 170. If the apparatus is still in the "Prime" state, the apparatus determines 166 whether the rotor speed exceeds a predetermined minimum speed. It has been found that cellular blood components can drift into undesired parts of the separation vessel, if the rotor speed is too low to maintain a sufficiently high gravitational field. Drifting blood components would invalidate the hemolysis test. If the speed is too low, therefore, the test is disabled 170. If the conditions described above are met, however, a test 168 to identify hemolysis during priming can be run. After the test, the apparatus will continue 171 with other processes.

The test 168 to identify hemolysis during priming is illustrated in FIG. 6. This test should be conducted only when the apparatus is priming. Moreover, if the centrifuge speed is less than a predetermined minimum, for example less than 200 rpm, the test should not be run because of the possibility of fluid backing up through the tubes. The test 168 first confirms 172 initial conditions. If a R/G ratio of equal to or greater than 50 has not been observed previously and the first draw is not complete and the R/G ratio is currently equal to or greater than 50 (the initial conditions 172), an internal logging message may optionally be given 174, for example, "Checking for Prime Hemolysis will occur on First Return. R/G Ratio=XX", where XX is the measured ratio. A High R/G Ratio flag is set 176, indicating that a high R/G ratio had been observed during the first draw cycle.

Next, the test can proceed 178 if the High R/G Ratio flag has been set, and if the first draw cycle is complete but the first return cycle is NOT complete, that is, fluid is being returned to the donor for the first time. The final conditions 180 for detecting hemolysis during blood prime are if the R/G ratio is greater than or equal to a predetermined hemolysis R/G return ratio limit and the Green value is greater than or equal to a predetermined hemolysis Green limit. The limits are determined empirically and are dependent on the configuration of the particular apheresis machine implementing the present invention. Preferably, for the Trima Accel apheresis machine, for example, the hemolysis R/G return ratio limit should be one and one tenth (1.1) and the hemolysis Green limit should be one thousand (1000) reflectance units. If the final conditions 180 are met, a hemolysis condition is declared, and an alarm 182 is given. The alarm may require the operator to terminate the apheresis procedure. The test may also be discontinued. Otherwise, control is returned 184 from the test 168 to the prime hemolysis alarm program 150.

At steps 172 and 180 of the hemolysis test 168, the program receives data from the red/green sensor 74. This data comprises a ratio of intensity of the red light to the green light and an intensity of the green light (in step 180). The programming may check 186 the ratio value, as shown in FIG. 7, to avoid dividing by zero. Upon receiving a request to sample 188 the R/G ratio, if the Green value is not equal to zero (0) at step 190, the R/G ratio can be directly calculated 192. If the red value is also zero 194, the ratio may be set 196 to one (1). Otherwise the R/G ratio is set 198 to a large number, for example one million (1,000,000). The subroutine 186 will then return 200 with a red/green ratio value for use in the test 168 described above.

The improvement described herein allows an apheresis blood processing device to identify hemolysis during blood priming and to distinguish uncorrectable hemolysis from correctable spillover events.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such or other embodiments and with various modifications required by the particular application (s) or use(s) of the present invention. It is intended that the appended claims be construed to include alternative embodiments to the extent permitted by the prior art.

What is claimed is:

1. A method for detecting hemolysis in a centrifugal blood processing apparatus, said blood processing apparatus comprising a sensor detecting red light and green light, said method comprising
    detecting hemolysis during priming of said blood processing apparatus by identifying characteristic signals from said sensor, said step of detecting hemolysis comprising
        identifying a red/green light intensity ratio higher than a first pre-determined limit;
        identifying a second red/green intensity ratio higher than a second pre-determined limit during a first return cycle wherein fluids are being returned to a donor; and
        identifying a value of green light intensity higher than a third pre-determined limit; and
    initiating an alarm condition in response to detection of hemolysis.

2. The method of claim 1 wherein said first pre-determined limit is fifty.

3. The method of claim 1 wherein said second pre-determined limit is one and one tenth.

4. The method of claim 1 wherein detecting hemolysis further comprises
    identifying a red/green intensity ratio higher than a predetermined limit during a first return cycle wherein fluids are being returned to a donor.

5. The method of claim 1 wherein detecting hemolysis further comprises
    identifying a value of green light intensity higher than a pre-determined limit during a first return cycle wherein fluids are being returned to a donor.

\* \* \* \* \*